(12) United States Patent
Brinkhaus et al.

(10) Patent No.: US 8,939,921 B2
(45) Date of Patent: Jan. 27, 2015

(54) APPARATUS AND METHOD FOR DETECTING THE HAND FORCE OF THE HAND PRESSURE

(75) Inventors: Bernhard Brinkhaus, Oetwil an der Limmat (CH); Marco Schuurmans Stekhoven, Zurich (CH)

(73) Assignee: Msys AG, Hergiswil (CH)

( * ) Notice: Subject to any disclaimer, the term of this patent is extended or adjusted under 35 U.S.C. 154(b) by 227 days.

(21) Appl. No.: 13/543,017

(22) Filed: Jul. 6, 2012

(65) Prior Publication Data

US 2013/0023799 A1    Jan. 24, 2013

(30) Foreign Application Priority Data

Jul. 6, 2011 (EP) .................................... 11172948

(51) Int. Cl.
*A61B 5/00* (2006.01)

(52) U.S. Cl.
USPC .......................................................... 600/595

(58) Field of Classification Search
CPC .............................. A61B 5/224; A61B 5/225
USPC ...................... 600/557, 587, 595; 482/44, 49; 73/379.01–379.03
See application file for complete search history.

(56) References Cited

U.S. PATENT DOCUMENTS

| | | | | |
|---|---|---|---|---|
| 5,317,916 A * | 6/1994 | Kovacevic | ................. | 73/379.03 |
| 5,329,813 A * | 7/1994 | Lewis, Jr. | ................... | 73/379.03 |
| 5,643,138 A * | 7/1997 | Huang | .............................. | 482/4 |
| 5,662,123 A * | 9/1997 | Goldman | ...................... | 600/595 |
| 6,725,728 B1 * | 4/2004 | Lee | ................................. | 73/824 |
| 6,770,011 B1 * | 8/2004 | Hinds | ............................. | 482/44 |
| 8,128,541 B2 * | 3/2012 | Hartman | ....................... | 482/139 |
| 8,240,202 B2 * | 8/2012 | Wimer et al. | .............. | 73/379.03 |
| 2004/0243021 A1 | 12/2004 | Murphy | | |
| 2006/0063647 A1 | 3/2006 | Jones-Glaser | | |

FOREIGN PATENT DOCUMENTS

| | | |
|---|---|---|
| WO | WO2009/052100 | 4/2009 |
| WO | WO2011/080237 | 7/2011 |

* cited by examiner

*Primary Examiner* — Max Hindenburg
(74) *Attorney, Agent, or Firm* — Pearl Cohen Zedek Latzer Baratz LLP

(57) ABSTRACT

An apparatus for detecting hand force or hand pressure includes a longitudinally extending hollow body having an upper fixed end part, a lower fixed end part and a longitudinally extending spacer element that keeps the upper end part and the lower end part mutually spaced apart. The hollow body includes a flexible outer cover which connects the upper end part to the lower end part such that a closed inner space is formed within which the spacer element is also arranged. The outer cover is can be at least partly surrounded by a hand, and the inner space of the hollow body contains a gel, elastic multicomponent or liquid material which acts as a pressure transmitter. A pressure measuring apparatus extends at least partly in the inner space in the longitudinal direction to transmit the pressure from the outer cover via the pressure transmitter to the pressure measuring apparatus.

14 Claims, 4 Drawing Sheets

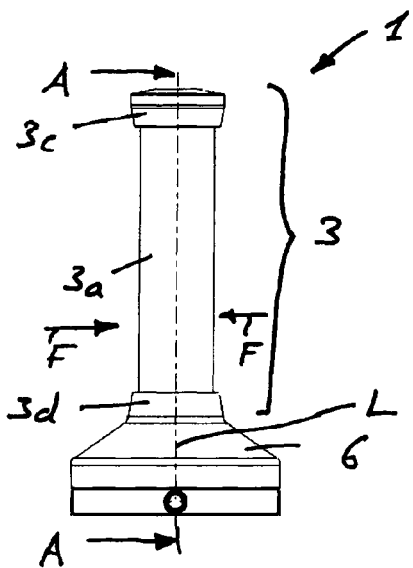
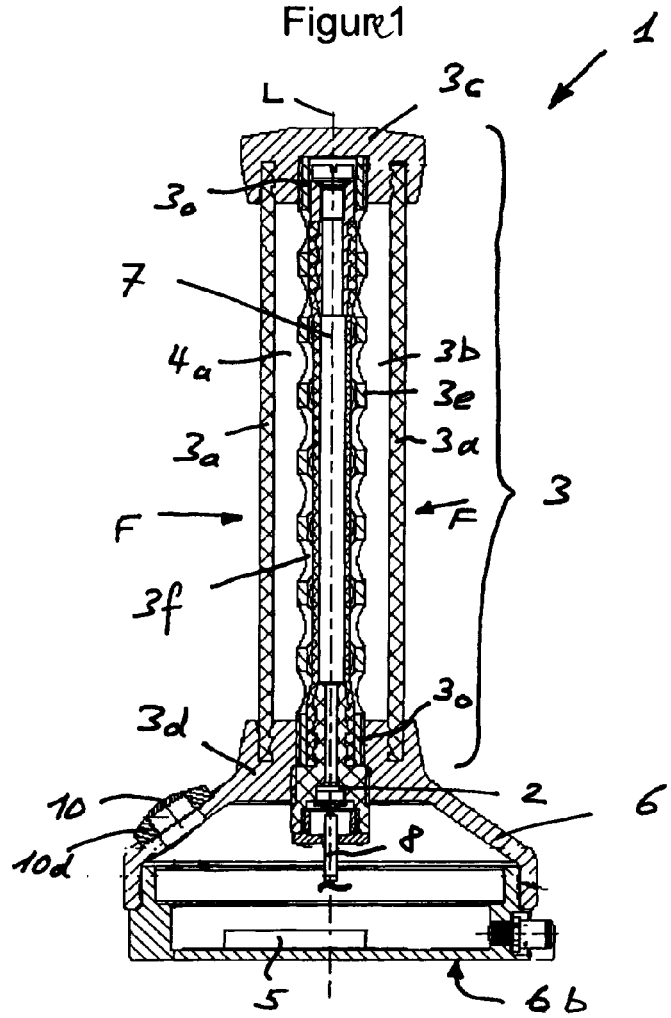
Figure 1
Figure 2 (A-A)

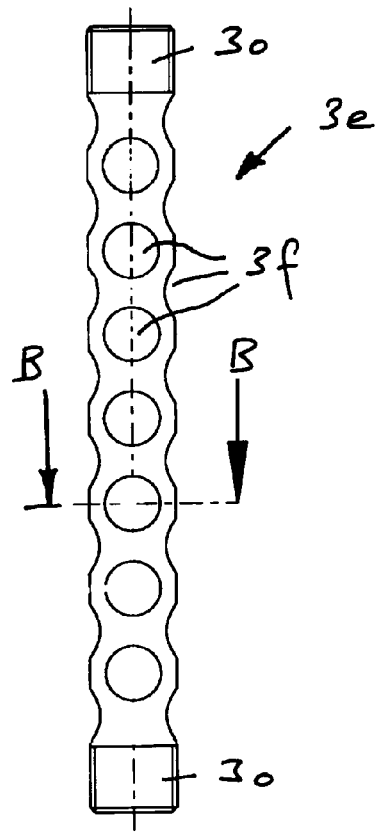
Figure 3
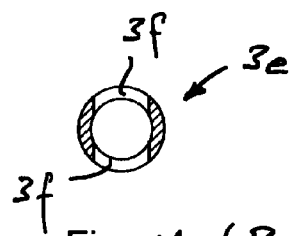
Figure 4 (B-B)
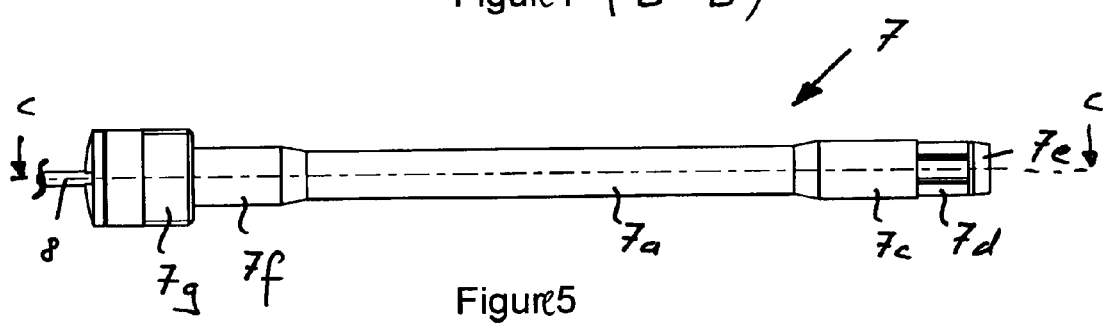
Figure 5

APPARATUS AND METHOD FOR DETECTING THE HAND FORCE OF THE HAND PRESSURE

CROSS-REFERENCE TO RELATED APPLICATIONS

This application claims priority from European Patent Application No. 11172948.9, filed Jul. 6, 2011, which is hereby incorporated by reference.

DESCRIPTION

The invention relates to an apparatus for detecting the hand force or the hand pressure and in particular the perception of pain. The invention further relates to a method of detecting the hand force or the hand pressure.

PRIOR ART

Pain is one of the most frequent reasons for consulting a physician, with pain representing a subjective feeling which includes sensory, cognitive and emotional aspects. An exact measurement of pain would therefore be extremely helpful, for example for pain monitoring, for a diagnosis or for adjusting pain medication therapy.

Document WO 2009/052100 discloses an apparatus for measuring pain. This apparatus has the disadvantage that the pain can only be measured with extreme imprecision and that the apparatus is only suitable to measure intestinal pain.

SUMMARY OF THE INVENTION

It has been shown that an exact detection of the hand force or of the hand pressure enables interesting possibilities for monitoring and treating people and that the exact detection of the hand force or the hand pressure is in particular suitable for detecting perceptions of pain of a person. An apparatus and a method for detecting and measuring pain of a person are disclosed in the application PCT/EP2010/070736 bearing the title "Apparatus and method for detecting and measuring pain" whose content is herewith included in this application.

This object is in particular satisfied by an apparatus for detecting the hand force or the hand pressure and in particular perceptions of pain of a person, comprising a pressure or force measuring apparatus and comprising a hollow body extending in a longitudinal direction, wherein the hollow body includes an upper fixed end part, a lower fixed end part and a spacer element, wherein the upper end part and the lower end part are kept mutually spaced apart via the spacer element, wherein the spacer element extends in the longitudinal direction, and wherein the hollow body includes a flexible outer cover which connects the upper end part to the lower end part such that a closed inner space is formed within which the spacer element is also arranged, wherein the outer cover is designed such that it can be at least partly surrounded by a hand, and wherein the inner space of the hollow body contains a gel material, an elastic multicomponent material or a liquid material which acts as a pressure transmitter (also known as a pressure seal or diaphragm seal), and wherein the pressure or force measuring apparatus extends at least partly in the inner space in the longitudinal direction to transmit the pressure from the outer cover via the pressure transmitter to the pressure or force measuring apparatus.

This object is further in particular satisfied by a method of detecting perceptions of pain or the pain intensity of a person, in that a cylindrical hollow body is at least partly surrounded by a hand, in that a pressure is exerted onto a flexible outer cover of the hollow body by pressing the hand closed, wherein the pressure is transmitted via a gel material, an elastic multicomponent material or a liquid material which acts as a pressure transmitter to a pressure or force measuring apparatus, wherein the elastic behavior of the flexible outer cover is set via the pressure of the pressure transmitter such that the diameter of the outer cover is maintained or is essentially maintained during the pressing; and wherein the pressure or the force measured by the pressure or force measuring apparatus is used as a measure for the pain perceived by the person.

The apparatus in accordance with the invention relates to the field of detecting and measuring the hand force or the hand pressure and in particular to the field of measuring pain and perceptions of pain of a person and their detection. The apparatus in accordance with the invention allows a hand force or a hand pressure to be measured exactly and in a reproducible manner, with the measured value particularly advantageously being used as a measure for pain or for the perception of pain.

In an advantageous embodiment, the apparatus in accordance with the invention also makes it possible to generate pain. A substantial advantage of the apparatus in accordance with the invention can be seen in the fact that it makes it possible to measure pain reproducibly and preferably to order its amount in specific levels. A person has the nature that he pulls back the hand by way of a reflex on pain, in particular on severe pain, with the palm of the hand being able to be contracted until a fist is formed To make use of this reflexive behavior of people, the apparatus in accordance with the invention is designed such that it has a hollow body which can be surrounded at least partly by a hand. The hollow body is designed in tubular form, in particular as a tube extending in a straight line, in a particularly advantageous embodiment. A hollow body of such a design sits easily in the hand and utilizes the natural, reflexive movement of the person to measure the hand force or the hand pressure or to measure pain in that the hand holds the hollow body more strongly and more powerfully in a natural manner as the pain increases. The surface of the hollow body which is designed to contact the hand should preferably be designed to be shape-stable, or substantially shape-stable, but should also feel pleasant, which produces the advantage that its shape does not change, or only changes slightly, independently of the engaging force of the hand. This allows the force effected by the hand to be measured in a reproducible and accurate manner. In other words, if the shape of the hollow body were to change due to the force effected on the hollow body by the hand, which would be the case, for example, with a rubber bellows filled with air, the perceived pain would no longer be measurable via the force effected by the hand since the rubber bellows yields as the force increases and changes its shape so that it is difficult or is no longer possible to express the perceived pain in a preferably linear manner via the force, in particular when the hand is already clenched to a fist. It can prove to be advantageous to design the surface of the hollow body such that no pronounced, and possibly even painful, pressure spots are formed at the hand surface which contacts the apparatus in accordance with the invention. Such pressure points are unpleasant and could even falsify the measurement. In an advantageous embodiment, the surface of the hollow body which is designed for contact with the hand has a specific elasticity to avoid such pressure points or pain points at the contacting hand. The apparatus in accordance with the invention makes it possible to measure the pressure or pressing force effected by the hand particularly accurately. The apparatus in accordance with the invention allows the strength of the perceived pain to be measured reliably and also reproducibly in an individual person.

The apparatus in accordance with the invention in particular has the advantage that the pain, and preferably also its states, can be detected exactly and that the measurements of the pain are objectively reproducible.

The invention will be described in the following with reference to embodiments.

BRIEF DESCRIPTION OF THE DRAWINGS

The drawings used to illustrate the embodiments show:
FIG. 1 a side view of an apparatus for detecting the hand force;
FIG. 2: a longitudinal section through FIG. 1 along the line A-A;
FIG. 3 a side view of a spacer element;
FIG. 4 a cross-section through FIG. 3 along the line B-B;
FIG. 5 a side view of a pressure measuring apparatus;
FIG. 7b schematically, a plan view of FIG. 7a.

DETAILED DESCRIPTION OF THE INVENTION

Figure 6:
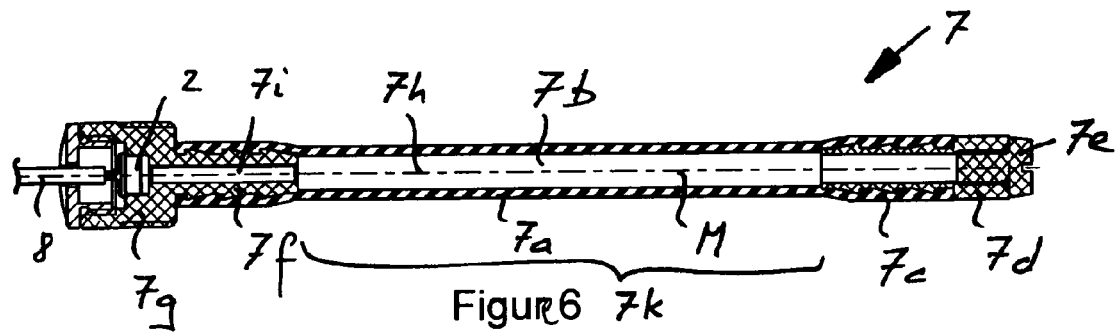
FIG. 6 a longitudinal section through the pressure measuring apparatus shown in FIG. 5 along the line C-C.

FIG. 1 shows an apparatus 1 for detecting the hand force or the hand pressure and in particular the perception of pain in a side view; FIG. 2 in a longitudinal section along the line A-A. The apparatus 1 comprises a hollow body 3 extending in a longitudinal direction L, wherein the hollow body 3 includes an upper fixed end part 3c, a lower fixed end part 3d and a spacer element 3e, wherein the upper end part 3c and the lower end part 3d are held mutually spaced apart via the spacer element 3e, with the spacer element 3c extending in the longitudinal direction L. The hollow body 3 includes a flexible outer cover 3a which connects the upper end part 3c to the lower end part 3d such that a closed inner space 3b is formed which is in particular fluid-tight, and within which the spacer element 3e is also arranged. The outer cover 3a is designed such that it can be surrounded at least in part by a hand in that the cross-section or the periphery of the outer cover 3a is selected in accordance with the size of a human hand. The upper and lower end parts 3c, 3d are of particular importance for the exact measurement since the supper and the lower end part 3c, 3d are fixed or rigid and prevent an escape or an increase in size of the inner space 3b in the direction of extent L. The apparatus 1 additionally includes a pressure or force measuring apparatus 7 which extends in the inner space 3b in the longitudinal direction L. The inner space 3b of the hollow body 3 contains or is filled with a gel material 4a, an elastic multicomponent material 4a or a liquid material 4a which acts as a pressure transmitter to transmit the pressure from the outer cover 3a via the pressure transmitter to the pressure or force measuring apparatus 7. A closed inner space 3b is understood as an inner space 3b which is closed toward the exterior such that the pressure transmitter, i.e. the gel material 4a, the elastic multicomponent material 4a or the liquid material 4a which is located in the inner space 3b cannot escape to the exterior from the apparatus 1. The inner space 3b is thus at least closed in a fluid-tight manner when a fluid is used as the pressure transmitter. In FIG. 2, the lower end part 3d has an aperture 3p which is designed as an internal thread into which the pressure measuring apparatus 7 is screwed. The pressure measuring apparatus 7 is connected to the aperture 3p and/or is sealed such that no discharge of the pressure transmitter via the aperture is possible.

The hollow body 3 thus surrounds a closed inner space 3b, with any passages in the upper and/or lower end parts 3c, 3d, for electrically conductive cable, for example, or for fastening the pressure measuring apparatus 7 as shown in FIG. 2, being sealed to form a closed inner space from which the pressure transmitter cannot escape.

The spacer element 3e which is shown in detail FIG. 3 in a side view and in FIG. 4 in a section along the line B-B is designed as a hollow tube having wall openings 3f, for example circular wall openings 3f, and comprises a fastening section 3o at the top and at the bottom which, as shown in FIG. 2, are fixedly connected to the upper end part 3c and to the lower end part 3d respectively to hold the two end parts 3c, 3d at a mutual defined distance. The wall openings 3f or wall passages can be designed in a plurality of forms to form a pressure conducting connection to the pressure or force measuring device 7 starting from the flexible outer cover 3a with the aid of the material located in the inner space 3b, e.g. a gel material 4a.

As shown in FIG. 2, the pressure or force measuring apparatus 7 is introduced through the lower end part 3d into the inner space of the spacer element 3e from below, with the pressure or force measuring apparatus 7 being screwed to the lower end part 3d and being fixedly held thereby. The pressure or force measuring apparatus 7 is shown in detail in FIGS. 5 and 6, with FIG. 5 showing a side view and FIG. 6 a section along a line C-C. As can be seen from FIG. 6, the pressure and force measuring apparatus 7 includes a flexible hollow body 7a which extends in the direction of extent M and which has an inner space 7b, with the flexible hollow body 7a having an upper end section 7c at the right which is fixedly connected, preferably in a fluid-tight manner, to an upper closure 7d. The opening of the upper closure 7d is closed by a screw 7e. The flexible hollow body 7a has a lower end section 7f at the left which is fixedly connected, preferably in a fluid-tight manner, to a lower closure 7g. A force transducer 2 is arranged in the lower closure 7g, with the lower closure 7g having a fluid-conducting passage 7i which connects the inner space 7b to the force transducer 2. The inner space 2b and the fluid conducting passage 2i are filled with a second liquid material. The force transducer 2 has a surface which extends perpendicular to the direction of extent M and which the second liquid material 7h contacts so that the force transducer 2 is coupled to the inner space 7b perpendicular to the direction of space M to measure the pressure of the second liquid material 7h. The force transducer 2 is connected to the electronic unit 5 shown in FIG. 2 via a cable 8. The wall of the flexible, tubular hollow body 7a transmits a pressure force applied outwardly along the section 7k to the liquid 7h located in the inner space 7b, with the force transducer 2 measuring the pressure or the force effected on the force transducer 2 by the liquid 7h. The hollow space 7a can only transmit the force along the section 7k from the outside to the inside since the hollow body 7a contacts the upper closure 7d or the lower closure 7g respectively along the upper end section 7c and along the lower end section 7f. The screw 7e serves inter alia to fill the inner space 7b completely with the liquid 7h and to close the inner space 7b in a fluid-tight manner again afterward. In an advantageous embodiment, the section 7k of the flexible hollow body 7a has a Shore hardness in the range between 10 and 20 in particular due to the second liquid material 7h. Oil is, for example, used as the liquid material 7h.

In a preferred embodiment, the force measuring apparatus 7 extends, as shown in FIG. 2, along the total length L of the inner space 3b and additionally along the lower end part 3d, with the section 7k only extending within the inner space 3b. In a further embodiment, the force measuring apparatus 7 could also be designed so that it does not extend along the total length L of the inner space 3b, but rather, for example, only along half the length L, or for example along three-quarters of the length L. In the most preferred embodiment, the force measuring apparatus 7 extends, as shown in FIG. 2, along the center or along the axis L. The force measuring apparatus 7 is preferably arranged, as shown, centered with respect to the longitudinal axis so that the forces applied to the flexible outer cover 3a are transmitted uniformly onto the pressure or force measuring apparatus 7. The pressure or force measuring apparatus 7 could, however, also be arranged extending eccentrically in the inner space 7b.

In a particularly advantageous embodiment, the flexible outer cover 3a is, as shown in FIGS. 1 and 2, designed in hollow cylindrical form. The flexible outer cover 3a is preferably made from silicone, vulcanized rubber or natural rubber. The gel material 4a, the elastic multicomponent material 4a or the liquid material 4a acting as a pressure transmitter transmits the pressure from the outer cover 3a onto the pressure or force measuring device 7. The pressure transmitter is advantageously filled into the inner space 3b at a predefined pressure on filling so that the pressure transmitter has a predefined pressure in a state of rest, that is without forces engaging at the outer cover 3a. The predefined filling pressure of the pressure transmitter influences the hardness or the resilience of the flexible outer cover 3a. In a particularly advantageous embodiment, the flexible outer cover 3a is selected from such a material and/or the predefined pressure of the pressure transmitter is selected such that the flexible outer cover 3a has a Shore hardness in the range between 20 and 90. The following can thus inter alia be achieved: On the one hand, the flexible outer cover 3a should feel pleasant to the contacting hand, which is achieved in that the flexible outer cover 3a or the pressure transmitter respectively has certain elastic properties. These elastic properties perceived as pleasing by the hand have the advantage that no pressure points result at the hand. A hard outer cover 3a would bring about pressure points at a hand being pressed together, which would have the consequence that the hand is partly relaxed again or that the force is reduced due to the pain or pressure which results. The avoidance of such pressure points is therefore of decisive importance for an exact measurement of the hand force, of the hand pressure or of perceptions of pain. On the other hand, it is particularly advantageous if the diameter of the flexible outer cover 3a only slightly varies even under larger engaging forces because it becomes more difficult for the hand contacting the outer cover 3a to effect a large force on the outer cover 3a the smaller the diameter of the flexible outer cover 3a becomes. The apparatus in accordance with the invention thus has the advantage in a particularly advantageous embodiment that the above-named properties of the outer cover 3a can be set or can be defined in advance via the filling pressure of the pressure transmitter.

FIG. 2 additionally shows a housing 6 with a standing surface 6b, with the lower fixed section 3d forming part of the housing 6. The lower fixed section 3d is arranged such that the hollow body 3 extends substantially perpendicular to the standing surface 6b. In addition, an electronic unit 5 is preferably arranged in the housing 6 and is connected to the force transducer 2 via the cable 8. A pain actuator 10 is preferably also arranged in the housing 6 and is designed as a heat generation apparatus.

Figure 10:
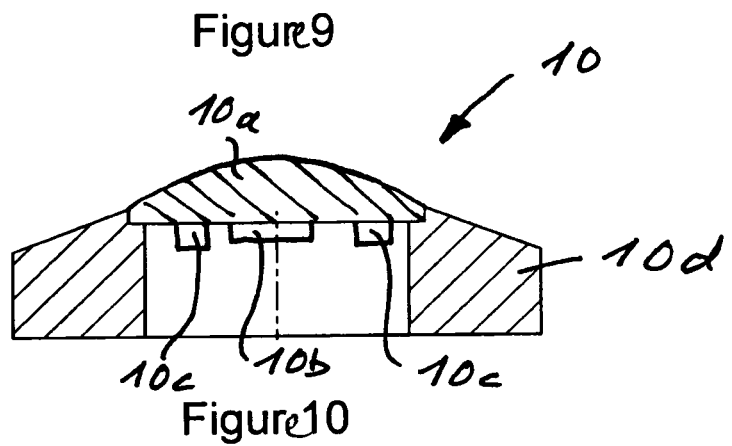
FIG. 10 a longitudinal section through a pain actuator.
Generally, the same parts are provided with the same reference numerals in the drawings.

FIG. 10 shows in a longitudinal section a pain actuator 10 having a metallic cover 10a at whose lower side a heating element 10c and a temperature sensor 10b are arranged. The electric lines to the electronic unit 5 are not shown.

Figure 7A:
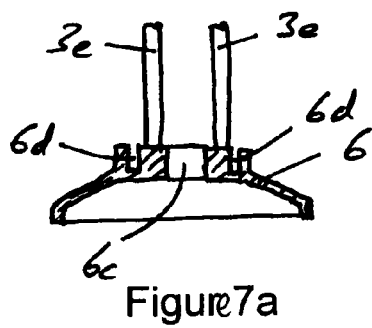
FIG. 7a schematically, a longitudinal section through a further embodiment of a housing with spacer elements.
Figure 7B:
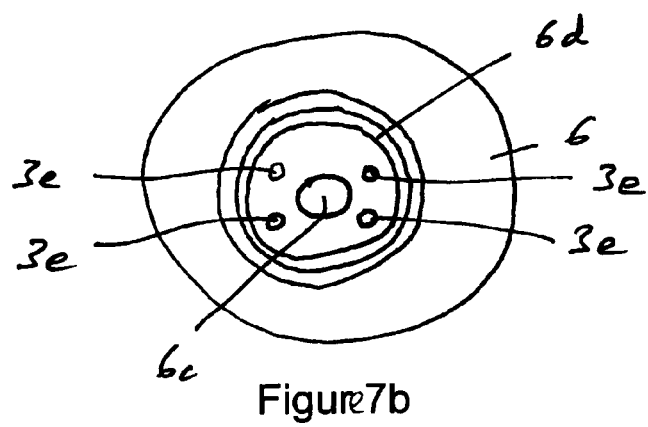

FIG. 7a shows schematically and only indicated in part a section through a housing 6 having a bore 6c and a recess 6d and FIG. 7b shows a plan view thereof. The spacer element 3e in the example shown is formed from four bars which extend in the direction of extent L and connect the upper end part 3c to the lower end part 3d. The spacer element 3e can be produced in a plurality of possibilities to effect this spacing apart.

Figure 8:
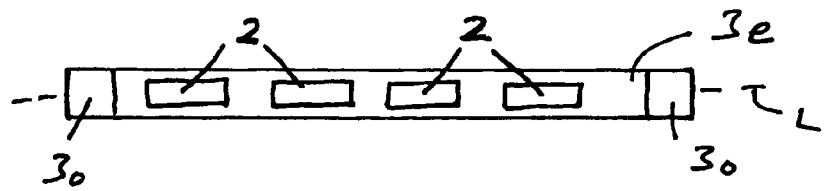
FIG. 8 schematically a side view of a further pressure measuring apparatus.

FIG. 8 schematically shows a spacer element 3e and a pressure or force measuring apparatus 7 in that a plurality of force transducers 2 are arranged at the spacer element 3e mutually spaced apart in the longitudinal direction L. Each force transducer 2 is connected to the electronic unit in a signal conductive manner so that the pressure applied by the pressure transmitter in the inner space 3b can be measured.

Figure 9:
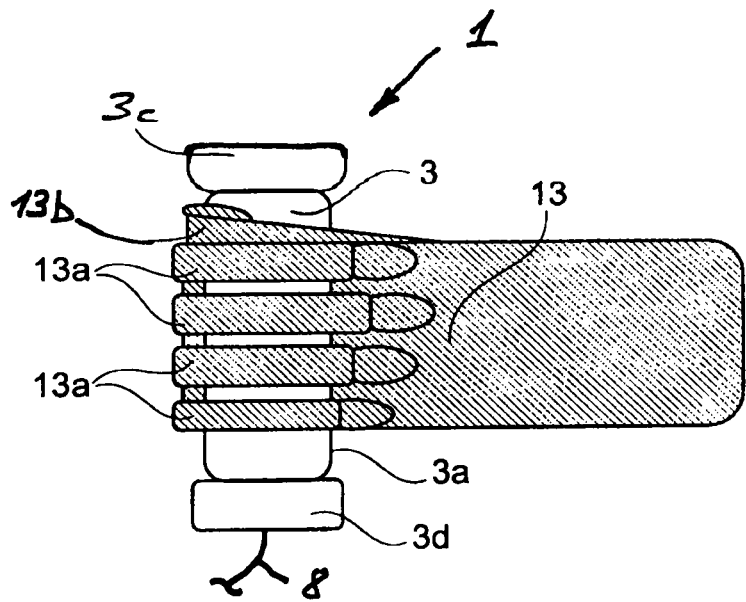
FIG. 9 schematically, a further embodiment of an apparatus for detecting the hand force with a hand surrounding it.

FIG. 9 schematically shows a further embodiment of the apparatus 1 in accordance with the invention comprising a hollow body 3 with an upper and a lower end part 3c, 3d and with a flexible outer cover 3a being arranged therebetween, with the apparatus 1, in contrast to the apparatus 1 shown in FIG. 2, not having any housing and the cable 8 being led to a downstream signal evaluation apparatus. FIG. 9 additionally schematically shows a hand 13 with fingers 13a and a thumb 19b which surround the flexible outer cover 3a.

The method of detecting perceptions of pain or the pain intensity of a person advantageously takes place in that a cylindrical hollow body 3 is at least partly surrounded by a hand, in that a pressure is exerted onto a flexible outer cover 3a of the hollow body 3 by pressing the hand closed, wherein the pressure is transmitted via a gel material, an elastic multicomponent material or a liquid material 4a, 4b which acts as a pressure transmitter to a pressure or force measuring apparatus 7 arranged in the hollow body 3, wherein the elastic behavior of the flexible outer cover 7a is set via the pressure of the pressure transmitter such that the diameter of the outer cover 3a is maintained or is essentially maintained during the pressing, and wherein the pressure or the force measured by the pressure or force measuring apparatus 7 is used as a measure for the pain perceived by the person.

The method can additionally take place in that a pain actuator 10 which heats up increasingly is touched and in that the measured pressure or the measured force is detected as a function of the temperature of the pain actuator 10. The temperature increase advantageously takes place overall by a predefined amount in the range of 1 to 5° C.

The invention claimed is:

1. An apparatus for detecting the hand force or the hand pressure of a person, comprising:
    a pressure or force measuring apparatus,
    a pain actuator, designed as a heat generation apparatus, and
    a hollow body extending in a longitudinal direction,
    wherein the hollow body includes an upper fixed end part, a lower fixed end part and a spacer element,
    wherein the upper end part and the lower end part are kept mutually spaced apart via the spacer element,
    wherein the spacer element extends in the longitudinal direction, and
    wherein the hollow body includes a flexible outer cover which connects the upper end part to the lower end part such that a closed inner space is formed within which the spacer element is also arranged, wherein the outer cover is designed such that it can be at least partly surrounded by a hand, and wherein the inner space of the hollow body includes a gel material, an elastic multicomponent material or a liquid material which acts as a pressure transmitter, and wherein the pressure or force measuring apparatus extends at least partly in the inner space in the longitudinal direction to transmit the pressure from the outer cover via the pressure transmitter to the pressure or force measuring apparatus.

2. The apparatus in accordance with claim 1, wherein the force measuring apparatus extends at least along the total length of the inner space.

3. The apparatus in accordance with claim 1, wherein the pressure or force measuring apparatus extends along the center of the hollow body.

4. The apparatus in accordance with claim 1,
wherein the spacer element is designed as a hollow tube with wall openings; and
wherein the pressure or force measuring apparatus is arranged extending within the spacer element.

5. The apparatus in accordance with claim 4, wherein the spacer element extends along the center axis of the hollow body.

6. The apparatus in accordance with claim 1, wherein the flexible outer cover is designed in the form of a hollow cylinder.

7. The apparatus in accordance with claim 1, wherein the hardness or the resilience of the flexible outer cover can be determined via the pressure of the pressure transmitter.

8. The apparatus in accordance with claim 6, wherein the flexible outer cover has a Shore hardness in the range between 20 and 90.

9. The apparatus in accordance with claim 1, wherein the pressure or force measuring apparatus includes a force transducer and a flexible hollow body which extends in a straight line in the direction of extent and which has an inner space;
wherein the inner space is closed and includes a second liquid material; and
wherein the force transducer is coupled perpendicular to the direction of extent toward the inner space to measure the pressure of the second liquid material.

10. The apparatus in accordance with claim 1, wherein the pressure or force measuring apparatus includes a plurality of force transducers which are arranged at the spacer element mutually spaced apart in the longitudinal direction.

11. The apparatus in accordance with claim 1,
wherein the lower fixed end part forms part of a housing;
wherein the housing has a standing surface; and
wherein the lower fixed end part is arranged such that the hollow body extends substantially perpendicular to the standing surface.

12. The apparatus in accordance with claim 11, wherein the pain actuator includes a metallic cover at whose lower side a heating element and a temperature sensor are arranged.

13. The apparatus in accordance with claim 11, wherein the pain actuator is arranged at the housing.

14. A method of detecting the hand force or the hand pressure of a person, comprising:
providing a cylindrical hollow body, which is at least partly surrounded by a hand,
increasingly heating a pain actuator which is touched by the hand,
allowing a pressure to be exerted onto a flexible outer cover of the hollow body by pressing the hand closed,
allowing the pressure to be transmitted via a gel material, an elastic multicomponent material or a liquid material to a pressure or force measuring apparatus arranged in the hollow body,
wherein the elastic behavior of the flexible outer cover is set via the pressure of the pressure transmitter such that the diameter of the outer cover is maintained or is essentially maintained during the pressing;
measuring the pressure or the force by the pressure or force measuring apparatus; and
detecting the measured pressure or the measured force as a function of the temperature of the pain actuator.

* * * * *